United States Patent [19]

Marugg et al.

[11] Patent Number: 5,420,021
[45] Date of Patent: May 30, 1995

[54] PROCESS FOR THE PREPARATION OF α-ACETOLACTIC ACID

[75] Inventors: John D. Marugg, Utrecht; Maria Y. Toonen, Vlaardingen; Walter M. M. Verhue, Oostvoorne; Cornelis T. Verrips, Maassluis, all of Netherlands

[73] Assignee: Unilever Patent Holdings B.V., Rotterdam, Netherlands

[21] Appl. No.: 839,433

[22] Filed: Feb. 24, 1992

[30] Foreign Application Priority Data

Feb. 22, 1991 [EP] European Pat. Off. ........... 91200379

[51] Int. Cl.$^6$ .................. C12P 19/00; C12N 15/00; C12N 1/00
[52] U.S. Cl. ............................. 435/74; 435/320.1; 435/252.3; 435/252.32; 435/252.9; 435/253.4; 435/885
[58] Field of Search .................. 435/74, 885, 320.1, 435/252.3, 252.32, 253.4, 252.9

[56] References Cited

U.S. PATENT DOCUMENTS 4,828,994 5/1989 Fahnestock et al. ............ 435/172.3

FOREIGN PATENT DOCUMENTS 0204326 6/1986 European Pat. Off. .
247646 12/1987 European Pat. Off. .
356739 3/1990 European Pat. Off. .

OTHER PUBLICATIONS

Goelling, et al., "Cloning and Expression of an A-Acetolactate Decarboxylas Gene from *Streptococcus lactis* subsp. diacetylactis in *Escherichia coli*", Appl. Env. Microb., vol. 54, No. 7, Jul. 1988, pp. 1889–1891.
Falco et al Nucleic Acids Res. vol. 13 (11) pp. 4011–4027 issued 1985.
Glover *Gene Cloning* Chapman and Hall Ltd., New York, N.Y. 1984 Chapter 7 pp. 158–163.

*Primary Examiner*—Robert A. Wax
*Assistant Examiner*—D. Schmickel
*Attorney, Agent, or Firm*—Cushman Darby & Cushman

[57] ABSTRACT

The invention relates to a process for the production of α-acetolactate and/or diacetyl, wherein a recombinant micro-organism containing an α-acetolactate synthase-encoding sequence is incubated in a medium containing an α-acetolactate precursor. The invention also provides a recombinant vector comprising a nucleotide sequence coding for an enzyme, which vector upon transfer into a host micro-organism enables expression of the nucleotide sequence in the host micro-organism, wherein the enzyme has α-acetolactate synthase activity.

8 Claims, 14 Drawing Sheets

Fig. IA

SEQUENCE TYPE: nucleotide with corresponding protein
SEQUENCE LENGTH: 2538 base pairs STRANDEDNESS: single
TOPOLOGY: linear
MOLECULAR TYPE: genomic DNA
ORIGINAL SOURCE ORGANISM: Lactococcus lactis
FEATURES: 550 to 2214 bp mature peptide
PROPERTIES: α-acetolactate synthase gene

```
CTGCAGCAGA ACGTTATCTC GTGGATGCTT TAAATTTACC AGAATTACAT GACGAAACAG    60
TCTTTTTGCT TGCTAATTTA TACTTCAACG AAGAAGATTT TGAAGCTGTC ATTAATCTTG   120
AAGAGCTTTT AGAAGATGAA CATTTATTAG CTAAATGGCT TTTTGCAGGA GCACATAAAG   180
CTTTGGAAAA TGATTCTGAA GCGGCTGCTT TGTATGAAGA ACTCATTCAA ACCAATCTGT   240
CAGAGAATCC AGAGTTTTTA GAAGACTATA TTGATTTTCT TAAAGAAATT GGTCAAATTT   300
CTAAAACAGA ACCAATTATT GAACAATATT TGGAACTTGT TCCAGATGAT GAAAATATGA   360
GAAATTTACT GACAGACTTA AAAAATAATT ACTGACAAAG CTGTCAGTAA TTATTTTTAT   420
TGTAAGCTAG AAAATTCAAA AACTTGCGTC AAAATAATTG TAAAAGGTTC TATTATCTGA   480
TAAAATGATT GTGAAGTAAT CCAAGAGATT ATGAAATATG AATTAGAACA AATAGAGGTA   540
```

```
AAATAAAAA  ATG TCT GAG AAA CAA TTT GGG GCG AAC TTG GTT GTC GAT AGT    591
           Met Ser Glu Lys Gln Phe Gly Ala Asn Leu Val Val Asp Ser
             1               5                  10

TTG ATT AAC CAT AAA GTG AAG TAT GTA TTT GGG ATT CCA GGA GCA AAA         639
Leu Ile Asn His Lys Val Lys Tyr Val Phe Gly Ile Pro Gly Ala Lys
 15              20                  25                  30

ATT GAC CGG GTT TTT GAT TTA TTA GAA AAT GAA GAA GGC CCT CAA ATG         687
Ile Asp Arg Val Phe Asp Leu Leu Glu Asn Glu Glu Gly Pro Gln Met
                 35                  40                  45

GTC GTG ACT CGT CAT GAG CAA GGA GCT GCT TTC ATG GCT CAA GCT GTC         735
Val Val Thr Arg His Glu Gln Gly Ala Ala Phe Met Ala Gln Ala Val
         50                  55                  60

GGT CGT TTA ACT GGC GAA CCT GGT GTA GTA GTT GTT ACG AGT GGG CCT         783
Gly Arg Leu Thr Gly Glu Pro Gly Val Val Val Val Thr Ser Gly Pro
         65                  70                  75

GGT GTA TCA AAC CTT GCG ACT CCG CTT TTG ACC GCG ACA TCA GAA GGT         831
Gly Val Ser Asn Leu Ala Thr Pro Leu Leu Thr Ala Thr Ser Glu Gly
         80                  85                  90

GAT GCT ATT TTG GCT ATC GGT GGA CAA GTT AAA CGA AGT GAC CGT CTT         879
Asp Ala Ile Leu Ala Ile Gly Gly Gln Val Lys Arg Ser Asp Arg Leu
 95                 100                 105                 110

AAA CGT GCG CAC CAA TCA ATG GAT AAT GCT GGA ATG ATG CAA TCA GCA         927
Lys Arg Ala His Gln Ser Met Asp Asn Ala Gly Met Met Gln Ser Ala
                 115                 120                 125

ACA AAA TAT TCA GCA GAA GTT CTT GAC CCT AAT ACA CTT TCT GAA TCA         975
Thr Lys Tyr Ser Ala Glu Val Leu Asp Pro Asn Thr Leu Ser Glu Ser
         130                 135                 140
```

Fig. 1B

```
ATT GCC AAC GCT TAT CGT ATT GCA AAA TCA GGA CAT CCA GGT GCA ACT        1023
Ile Ala Asn Ala Tyr Arg Ile Ala Lys Ser Gly His Pro Gly Ala Thr
        145                 150                 155

TTC TTA TCA ATC CCC CAA GAT GTA ACG GAT GCC GAA GTA TCA ATC AAA        1071
Phe Leu Ser Ile Pro Gln Asp Val Thr Asp Ala Glu Val Ser Ile Lys
        160                 165                 170

GCC ATT CAA CCA CTT TCA GAC CCT AAA ATG GGG AAT GCC TCT ATT GAT        1119
Ala Ile Gln Pro Leu Ser Asp Pro Lys Met Gly Asn Ala Ser Ile Asp
175                 180                 185                 190

GAC ATT AAT TAT TTA GCA CAA GCA ATT AAA AAT GCT GTA TTG CCA GTA        1167
Asp Ile Asn Tyr Leu Ala Gln Ala Ile Lys Asn Ala Val Leu Pro Val
                195                 200                 205

ATT TTG GTT GGA GCT GGT GCT TCA GAT GCT AAA GTC GCT TCA TCC TTG        1215
Ile Leu Val Gly Ala Gly Ala Ser Asp Ala Lys Val Ala Ser Ser Leu
                210                 215                 220

CGT AAT CTA TTG ACT CAT GTT AAT ATT CCT GTC GTT GAA ACA TTC CAA        1263
Arg Asn Leu Leu Thr His Val Asn Ile Pro Val Val Glu Thr Phe Gln
                225                 230                 235

GGT GCA GGG GTT ATT TCA CAT GAT TTA GAA CAT ACT TTT TAT GGA CGT        1311
Gly Ala Gly Val Ile Ser His Asp Leu Glu His Thr Phe Tyr Gly Arg
        240                 245                 250

ATC GGT CTT TTC CGC AAT CAA CCA GGC GAT ATG CTT CTG AAA CGT TCT        1359
Ile Gly Leu Phe Arg Asn Gln Pro Gly Asp Met Leu Leu Lys Arg Ser
255                 260                 265                 270

GAC CTT GTT ATT GCT GTT GGT TAT GAC CCA ATT GAA TAT GAA GCT CGT        1407
Asp Leu Val Ile Ala Val Gly Tyr Asp Pro Ile Glu Tyr Glu Ala Arg
                275                 280                 285

AAC TGG AAT GCA GAA ATT GAT AGT CGA ATT ATC GTT ATT GAT AAT GCC        1455
Asn Trp Asn Ala Glu Ile Asp Ser Arg Ile Ile Val Ile Asp Asn Ala
                290                 295                 300

ATT GCT GAA ATT GAT ACT TAC TAC CAA CCA GAG CGT GAA TTA ATT GGT        1503
Ile Ala Glu Ile Asp Thr Tyr Tyr Gln Pro Glu Arg Glu Leu Ile Gly
        305                 310                 315

GAT ATC GCA GCA ACA TTG GAT AAT CTT TTA CCA GCT GTT CGT GGC TAC        1551
Asp Ile Ala Ala Thr Leu Asp Asn Leu Leu Pro Ala Val Arg Gly Tyr
320                 325                 330

AAA ATT CCA AAA GGA ACA AAA GAT TAT CTC GAT GGC CTT CAT GAA GTT        1599
Lys Ile Pro Lys Gly Thr Lys Asp Tyr Leu Asp Gly Leu His Glu Val
335                 340                 345                 350

GCT GAG CAA CAC GAA TTT GAT ACT GAA AAT ACT GAA GAA GGT AGA ATG        1647
Ala Glu Gln His Glu Phe Asp Thr Glu Asn Thr Glu Glu Gly Arg Met
                355                 360                 365
```

Fig. 1C

| | |
|---|---|
| CAC CCT CTT GAT TTG GTC AGC ACT TTC CAA GAA ATC GTC AAG GAT GAT<br>His Pro Leu Asp Leu Val Ser Thr Phe Gln Glu Ile Val Lys Asp Asp<br>370 375 380 | 1695 |
| GAA ACA GTA ACC GTT GAC GTA GGT TCA CTC TAC ATT TGG ATG GCA CGT<br>Glu Thr Val Thr Val Asp Val Gly Ser Leu Tyr Ile Trp Met Ala Arg<br>385 390 395 | 1743 |
| CAT TTC AAA TCA TAC GAA CCA CGT CAT CTC CTC TTC TCA AAC GGA ATG<br>His Phe Lys Ser Tyr Glu Pro Arg His Leu Leu Phe Ser Asn Gly Met<br>400 405 410 | 1791 |
| CAA ACA CTC GGA GTT GCA CTT CCT TGG GCA ATT ACA GCC GCA TTG TTG<br>Gln Thr Leu Gly Val Ala Leu Pro Trp Ala Ile Thr Ala Ala Leu Leu<br>415 420 425 430 | 1839 |
| CGC CCA GGT AAA AAA GTT TAT TCA CAC TCT GGT GAT GGA GGC TTC CTT<br>Arg Pro Gly Lys Lys Val Tyr Ser His Ser Gly Asp Gly Gly Phe Leu<br>435 440 445 | 1887 |
| TTC ACA GGG CAA GAA TTG GAA ACA GCT GTA CGT TTG AAT CTT CCA ATC<br>Phe Thr Gly Gln Glu Leu Glu Thr Ala Val Arg Leu Asn Leu Pro Ile<br>450 455 460 | 1935 |
| GTT CAA ATT ATC TGG AAT GAC GGC CAT TAT GAT ATG GTT AAA TTC CAA<br>Val Gln Ile Ile Trp Asn Asp Gly His Tyr Asp Met Val Lys Phe Gln<br>465 470 475 | 1983 |
| GAA GAA ATG AAA TAT GGT CGT TCA GCA GCC GTT GAT TTT GGC TAT GTT<br>Glu Glu Met Lys Tyr Gly Arg Ser Ala Ala Val Asp Phe Gly Tyr Val<br>480 485 490 | 2031 |
| GAT TAC GTA AAA TAT GCT GAA GCA ATG AGA GCA AAA GGT TAC CGT GCA<br>Asp Tyr Val Lys Tyr Ala Glu Ala Met Arg Ala Lys Gly Tyr Arg Ala<br>495 500 505 510 | 2079 |
| CAC AGC AAA GAA GAA CTT GCT GAA ATT CTC AAA TCA ATC CCA GAT ACT<br>His Ser Lys Glu Glu Leu Ala Glu Ile Leu Lys Ser Ile Pro Asp Thr<br>515 520 525 | 2127 |
| ACT GGA CCG GTG GTA ATT GAC GTT CCT TTG GAC TAT TCT GAT AAC ATT<br>Thr Gly Pro Val Val Ile Asp Val Pro Leu Asp Tyr Ser Asp Asn Ile<br>530 535 540 | 2175 |
| AAA TTA GCA GAA AAA TTA TTG CCT GAA GAG TTT TAT TGA TTACAATCAA<br>Lys Leu Ala Glu Lys Leu Leu Pro Glu Glu Phe Tyr -<br>545 550 | 2224 |
| GCAATTTGTG GCATAACAAA ATAAAAGAAG AAGGCCTTGA ACACCTAAGC GTTCAGGGCC | 2284 |
| TTTTTTTGTG AAATAAATTA GATGAAATTT ACAATGAGTT TTGTGAAACT AGCTTCTAGT | 2344 |
| TTGTGAAAAA TTGCCTATAA TTGCCGAATA AAAATACCCA TTTACCACTC CAAGAGGATG | 2404 |
| CTTCAAATTA GCTAAATACC CGTTTTAGAG GATGCGTAAA AACAACAAAA GAGGATGAGT | 2464 |
| ATAGAACGAT AAAACTTTTT TATGATAGGT TGAGAGAATT GAATATAAAA TATAATAAGT | 2524 |
| AGAAGGCAGC AATT | 2538 |

PROCESS FOR THE PREPARATION OF α-ACETOLACTIC ACID

The present invention is in the field of food flavorings. The invention relates in particular to a process for the production of α-acetolactic acid (2-hydroxy-2-methyl-3-oxobutanoic acid) and/or diacetyl (2,3-butanedione).

For many years already, diacetyl has been used as a flavoring additive, e.g. for butter-like products. Since diacetyl is very volatile, it will gradually escape from a flavored food product, thus limiting its direct use as a flavoring substance. Alpha-acetolactic acid (also referred to herein as α-acetolactate) is a diacetyl precursor which can slowly release diacetyl by oxidative decarboxylation. Therefore α-acetolactic acid can be used as an indirect flavoring substance having a prolonged flavoring effect. Due to its limited stability, in particular in liquid medium, and due to its difficult preparation resulting in products having a low α-acetolactic acid content, however, a large-scale use of α-acetolactic acid for flavoring purposes has not been possible thus far.

A process for the preparation of an aroma composition containing α-acetolactic acid is known from European Patent application 247.646. According to that process, a pasteurised milk product is fermented with a culture of Streptococcus diacetylactis under conditions which decrease the conversion of α-acetolactic acid. Typically, a product containing 0.01% to 0.1% of α-acetolactic acid can be obtained using this known process. An improved process for producing an aroma composition containing over 0.4% of α-acetolactic acid by fermentation with pretreated lactic acid bacteria is described in European Patent application 91202042.7.

It has been found now that α-acetolactic acid and/or derivatives thereof can be produced in high yields by using recombinant techniques. Accordingly, the present invention, in its first aspect, relates to a process wherein a recombinant micro-organism containing an α-acetolactate synthase encoding sequence is incubated in a medium containing an α-acetolactic acid precursor.

The α-acetolactate synthase encoding sequence contained in the micro-organism preferably comprises the nucleotide sequence essentially corresponding to the sequence 550–2211 of the appending FIG. 1 (SEQ ID NO: 1). The sequence is preferably incorporated in the genome of the micro-organism, in a single copy or in multiple copies, but it may also be contained e.g. in a plasmid in the micro-organism.

"Essentially corresponding to the sequence" is understood as to include genetic variants, such as hybrid sequences containing an α-acetolactate synthase encoding sequence coupled to homologous or heterologous regulatory regions, sequences encoding mutant α-acetolactate synthase proteins, and degenerate sequences. The nucleotide sequence may also be a sequence having mutations, including mutations which still allow hybridization with α-acetolactate synthase encoding sequences and genetic variants thereof, or which, on expression, still yield a protein with α-acetolactate synthase activity.

The recombinant micro-organism to be used in the process according to the invention preferably does not exhibit substantial α-acetolactate decarboxylase activity. This may be achieved by using a micro-organism wherein α-acetolactate decarboxylase activity is substantially reduced or absent, e.g. by a deletion, an insertion, a substitution or a mutation in its α-acetolactate decarboxylase encoding region. Substantially reduced activity is to be understood as being less than 50% of the original activity, preferably less than 20%, more preferably less than 10% of the original activity and most preferably no detectable activity.

The α-acetolactate precursor present in the medium of the process according to the invention may be pyruvic acid, pyruvate, citric acid and/or citrate and/or precursors thereof, such as oxaloacetic acid, lactic acid, lactose etc. It is noted that wherever an organic acid is mentioned in this specification, this shall be understood to comprise both the free acid and the anion and any salts thereof; similarly, where the anion of an organic acid is mentioned, this also covers the acid and any salts. Preferably, the medium wherein α-acetolactate is produced contains pyruvate and/or citrate.

In a second aspect, the present invention relates to a recombinant vector comprising a nucleotide sequence coding for α-acetolactate synthase. Another aspect of the invention is concerned with a micro-organism capable of making α-acetolactate synthase, into which micro-organism a recombinant vector of the latter type has been introduced.

Alpha-acetolactate synthase is an enzyme which catalyses the conversion of pyruvic acid into α-acetolactic acid.

We have succeeded in isolating a gene coding for α-acetolactate synthase properties from Lactococcus lactis sp. lactis vat. diacetylactis. We have introduced this gene into vectors, so-called recombinant expression plasmids, which were successfully used to express the gene in micro-organisms.

Accordingly, the present invention is specifically concerned with a recombinant vector comprising a nucleotide sequence coding for an α-acetolactate synthase, which vector upon transfer into a host micro-organism enables the expression of α-acetolactate synthase and comprises an amino acid sequence which is essentially identical to the amino acid sequence given in FIG. 1 (SEQ ID NO: 2).

It is noted that the amino acid sequence represented in FIG. 1 can be modified without having a substantial adverse effect on the functionality, i.e. α-acetolactate synthase activity, of the polypeptide. Also it may be possible to improve the functionality of the polypeptide by introducing modifications into the amino acid sequence. Thus the present invention not only covers recombinant vectors comprising a nucleotide sequence coding for the above amino acid sequence, but also vectors comprising a nucleotide sequence coding for a different amino acid sequence which is still capable of converting pyruvate into α-acetolactate.

A quantitative measure of the similarity of amino acid sequences of α-acetolactate synthase enzymes is the percentage similarity calculated by means of the algorithm of Needleman and Wunsch as published in *J. Mol. Biol.* 48: 443–445 (1970). The percentage similarity can suitably be calculated using a computer programme named "Gap" which forms part of a sequence analysis software package (version 6.0) issued by G.C.G (see also Devereux et al. *Nucleic Acids Res.* 12: 387–395 (1984)). The percentage similarity between the amino acid sequence encoded by the nucleotide sequence of the vector according to the present invention, and any other unique sequence, as calculated using the algorithm of Needleman and Wunsch, generally exceeds 60%. More preferably this percentage similarity exceeds 75%, still more preferably 85%, and most preferably it exceeds 90%.

The gene coding for α-acetolactate synthase can suitably be cloned in a host micro-organism, using the present recombinant vector, thereby transforming the host micro-organism and/or its progeny to express the gene, resulting in the production of an enzyme having α-acetolactate synthase properties, optionally after further treatment of the protein produced. The present recombinant vector can be used to transform micro-organisms previously unable to make α-acetolactate into α-acetolactate producing micro-organisms. Alternatively said vector may be used to increase the α-acetolactate synthase activity of micro-organisms already capable of making α-acetolactate. When expression of the present gene in a micro-organism has been effected, said micro-organism can normally be reproduced using conventional fermentation techniques.

Whenever reference is made herein to the α-acetolactate synthase activity of an enzyme, what is meant is that said enzyme catalyses the formation of α-acetolactate in a pyruvate-containing α-acetolactate-free aqueous system. By catalysis is meant here that the formation of α-acetolactate is not observed in the absence of the enzyme and that the enzyme is not changed during the process.

It is noted that under processing conditions the α-acetolactate formed may be converted into diacetyl through oxidative decarboxylation. In order to arrive at the desired level of α-acetolactate activity, it is advisable to also monitor the amount of diacetyl and acetoin formed. Known analytical methods, such as $^{13}C$ NMR techniques, can be used for monitoring the production of α-acetolactate and diacetyl.

It is known that more than one codon may encode the same amino acid. Thus, generally there exist numerous nucleotide sequences coding for the same polypeptide. It will be appreciated by a skilled person that it is advantageous to adapt the codons of a heterologous gene in the preferred codon usage of the host cell. The nucleotide sequence of the gene encoding α-acetolactate synthase as obtained from Lactococcus lactis sp. lactis vat. diacetylactis is represented in FIG. 1 (SEQ ID NO: 1). It should be noted that slight deviations from the nucleotide sequence, even when affecting the amino acid sequence of the enzyme encoded therein, will not necessarily effect the functionality of said enzyme.

In addition to the nucleotide sequence coding for α-acetolactate synthase, the present recombinant vector comprises nucleotide sequences which enable the expression of the recombinant vector in host micro-organisms. Generally the present recombinant vector comprises:

(a) a double-stranded DNA (ds-DNA) coding for α-acetolactate synthase starting with a translational initiation codon, bound to the 5'-end of the coding region of the plus strand of the ds-DNA;

(b) an expression regulon situated upstream of the plus strand of the ds-DNA;

(c) a translational stop codon, bound to the 3'-end of the coding region of the plus strand of the ds-DNA, optionally followed by:

(d) a transcription termination sequence.

The present recombinant vector can suitably be introduced into bacteria or yeast in the form of a plasmid, i.e. an autonomously replicating, generally circular mini-chromosome. Alternatively the present recombinant vector can be integrated into the chromosomal DNA of bacteria, mould or yeast. The integration of the nucleotide sequence coding for α-acetolactate synthase into the chromosomal DNA offers the advantage that the transformed micro-organism will produce a progeny which is equally capable of forming α-acetolactate synthase.

In order to effect the integration of the nucleotide sequence coding for α-acetolactate synthase into the chromosomal DNA of a micro-organism, it is advantageous to additionally include in the present recombinant vector one or more nucleotide sequences which facilitate the integration of the gene coding for α-acetolactate synthase.

According to yet another preferred embodiment the present vector comprises (e) at least one DNA sequence derived from a food-grade organism coding for at least one enzyme that gives the transformed host micro-organism a selection advantage. Suitable examples are DNA sequences coding for enzymes involved in carbohydrate metabolism, more particularly in the metabolism of sugars such as lactose, sucrose and raffinose, e.g. phospho-β-galactosidase and α-galactosidase. Such DNA sequences are preferably obtained from food-grade organisms, in particular food-grade micro-organisms.

The present invention also encompasses a recombinant vector comprising a nucleotide sequence promoting α-acetolactate gene expression. In particular, this nucleotide sequence essentially corresponds to the sequence 1–549, in particular to the sequence 178–549 of FIG. 1 (SEQ ID NO: 1), or a part thereof. This vector may further contain a nucleotide sequence which encodes other valuable proteins, such as enzymes essential for metabolizing oligosaccharides, or which encodes proteases or peptidases or their maturases, or which encodes a food-grade natural bacteriocidal agent and/or immune proteins for such an agent and/or proteins involved in the proper secretion of such an agent.

Another aspect of the present invention relates to a micro-organism capable of producing α-acetolactate synthase, wherein the micro-organism is selected from the group consisting of a host micro-organism in which a recombinant vector as hereinbefore defined has been introduced and the progeny obtained from such a host micro-organism. The micro-organisms encompassed by the present invention include bacteria, moulds, yeasts etc. According to a preferred embodiment of the invention, the present micro-organism is a bacterium, more preferably said micro-organism is a food-grade bacterium. Most preferably the present micro-organism is selected from of genera Lactococcus, Streptococcus, Lactobacillus, Leuconostoc, Pediococcus, Bacillus, Bifidobacterium, Brevibacterium, Micrococcus, Propionibacterium, Staphylococcus, Streptococcus, Gluconobacter, Acetobacter, Vibrio costicola, Corynebacterium and Zymomonas.

According to a more preferred embodiment of the invention the present micro-organism is selected from the genera Lactococcus, Streptococcus, Lactobacillus, Leuconostoc, Bifidobacterium, Brevibacterium and Propionibacterium.

As a further preferred embodiment, the micro-organism has a substantially reduced α-acetolactate decarboxylase activity. This is achieved in particular by inactivating the α-acetolactate decarboxylase gene in the micro-organism, which is preferably selected from the genera Lactococcus, Streptococcus, Lactobacillus, Leuconostoc, Bifidobacterium, Brevibacterium and Propionibacterium.

The present micro-organisms can advantageously be used in the production of α-acetolactate or derivatives thereof (e.g. diacetyl) by growing said micro-organism under optimum conditions. Conditions which substantially affect the amount of α-acetolactate/diacetyl produced are temperature, composition of the growth medium and aeration. Generally the growth medium should mainly consist of water and contain a substrate selected from the group consisting of citrate, pyruvate and precursors thereof. Normally the growth medium additionally contains salts, and suitable sources of carbon and nitrogen to enable the micro-organism to grow.

Efficient production of α-acetolactate can be achieved in particular by (a) growth of the micro-organisms in an optimal medium or (b) reduced growth or even only maintenance of the micro-organisms thereby converting the substrate almost quantitatively into α-acetolactate.

The present micro-organism may suitably be used in a process for producing α-acetolactate and/or diacetyl, wherein the latter compounds are separated from the micro-organism, e.g. by centrifugation, ultra-filtration or distillation. Alternatively the complete composition obtained after fermentation with the present micro-organism can be used in for instance foodstuffs, optionally after evaporating the water therefrom. If used in the latter manner, the present micro-organism should be food-grade.

DESCRIPTION OF THE DRAWINGS

FIGS. 1A–1C shows the nucleotide sequence of the L. diacetylactis α-acetolactate synthase gene together with the deduced amino acid sequence (listed separately as SEQ ID NO: 1 and SEQ ID NO: 2, respectively, in the SEQUENCE LISTING).

The invention is illustrated by means of the following non-limiting examples:

EXAMPLE 1

Cloning and expression of the gene for α-acetolactate synthase in E. coli.

In order to identify genes involved in acetoin and/or diacetyl formation, a genomic library of Lactococcus lactis subsp. lactis biovar diacetylactis (L. diacetylactis) was constructed in plasmid vector pBR322 (Bolivar et al., Gene 2: 95–113 (1977)) in Escherichia coli. Therefore a preparation of total cell DNA of L. diacetylactis strain DSM20384 was partially digested with the restriction enzyme Sau3A, and subsequently ligated in plasmid pBR322 that was digested to completion with the restriction enzyme BamHI, essentially as has been described by Maniatis et al. (Molecular Cloning. A Laboratory Manual. Cold Spring Harbor Laboratory, Cold Spring Harbor, N.Y. 1982). The ligation mix was then used to transform E. coli SF8 cells selecting on LB agar plates supplemented with 100 μg/ml ampicillin.

Figure 2:
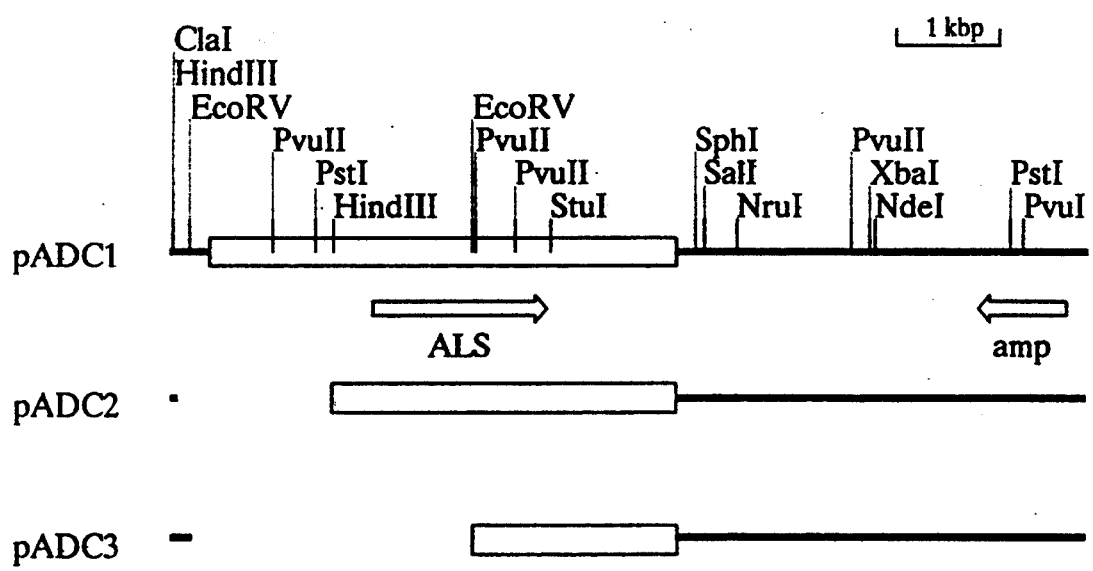
FIG. 2 shows the restriction enzyme maps of plasmid pADC1 and its deletion derivatives pADC2, and pADC3.

The Voges-Proskauer (VP) reaction (Krampitz, L. O., Methods Enzymol. 3: 271–283 (1957)) was used to screen E. coli transformants for the formation of acetoin when grown on pyruvate as the sole carbon source. Using this assay wild-type E. coli cells were found to be unable to produce acetoin. Among the more than 600 individual transformant clones carrying various fragments of the L. diacetylactis genome that were screened, one clone gave a positive VP reaction. The recombinant plasmid was isolated from this clone, and further characterized by restriction enzyme analysis (Goelling, D., and Stahl, U., Appl. Environ. Microbiol. 54: 1889–1891 (1988)). A restriction map of the plasmid, designated pADC1, is shown in FIG. 2.

Figure 3:
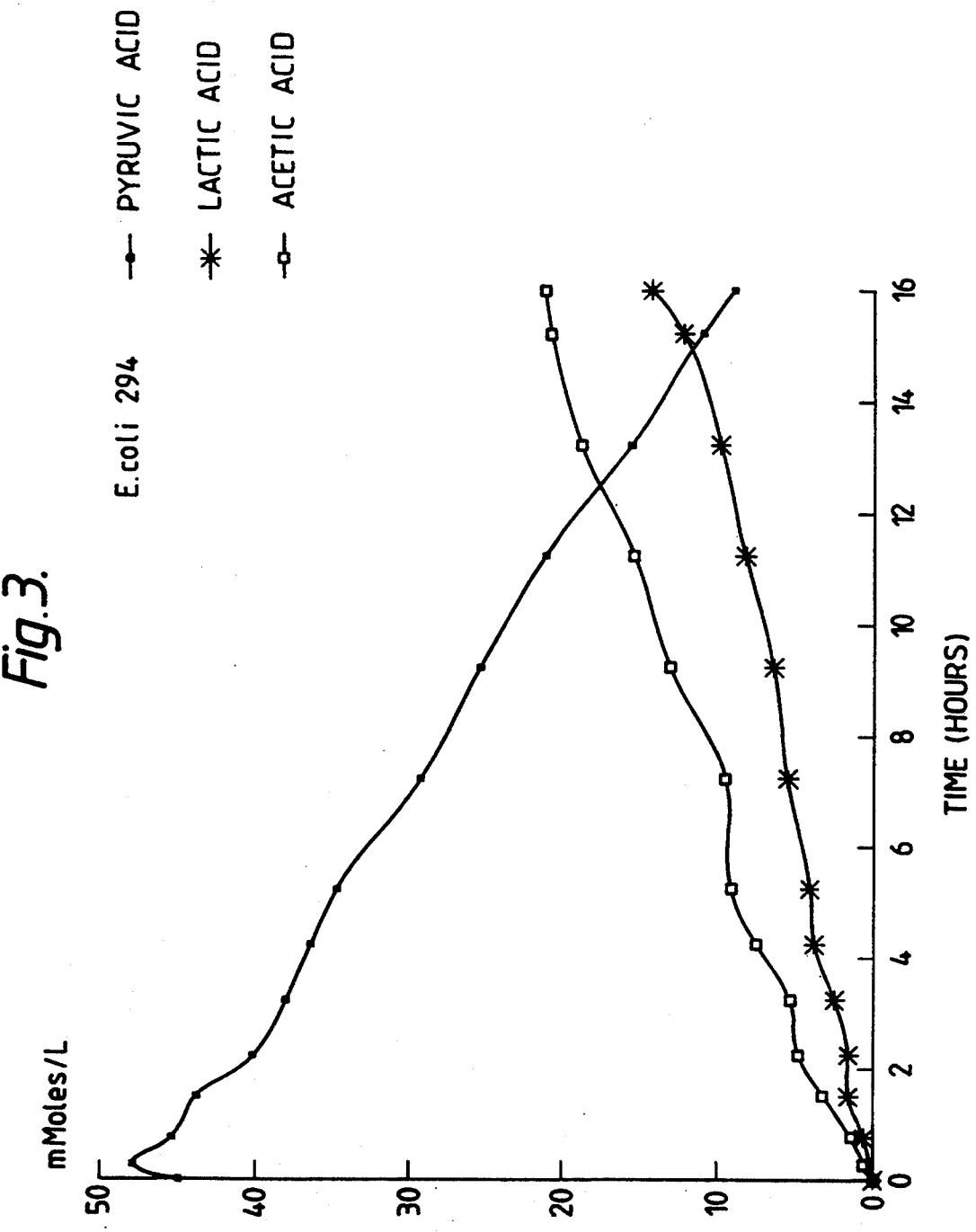
FIG. 3 shows concentrations of $^{13}$C-labelled pyruvate and its metabolites upon fermentation at 37° C. with E. coli 294.
Figure 4:
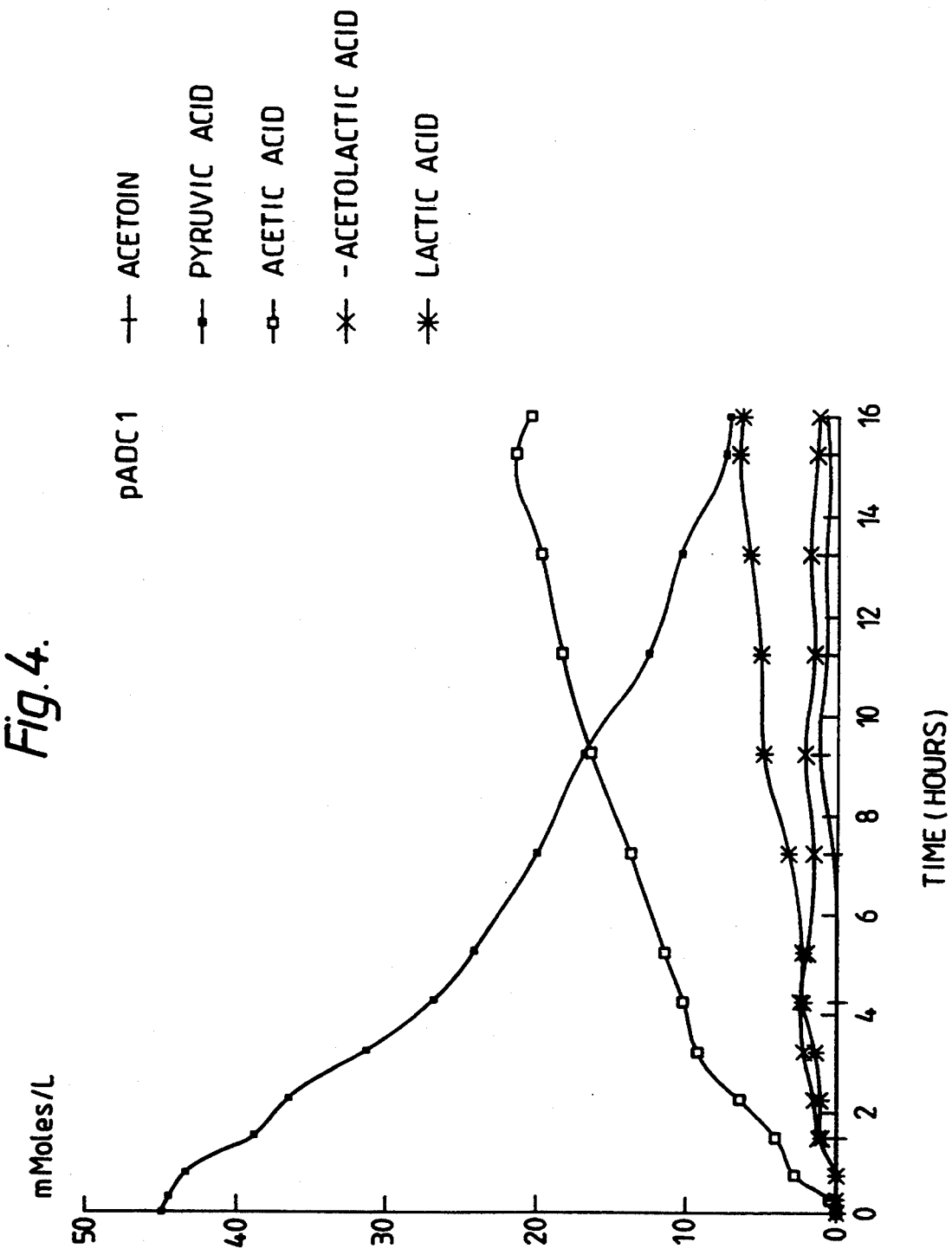
FIG. 4 shows concentrations of $^{13}$C-labelled pyruvate and its metabolites upon fermentation at 37° C. with E. coli 294(pADC1).

From this positive VP reaction Goelling and Stahl concluded to have cloned the L. diacetylactis gene for α-acetolactate decarboxylase (α-ALD) (Goelling, D., and Stahl, U., Appl. Environ. Microbiol. 54: 1889–1891 (1988)). However, acetoin formation from pyruvate is the result of two enzymic activities, i.e. α-acetolactate synthase (α-ALS) and α-ALD. To discriminate whether the production of acetoin by transformant E. coli(pADC1) cells results from α-ALS activity and/or from α-ALD activity encoded by the recombinant plasmid, the conversion of 3-$^{13}$C-labelled pyruvate was studied using the $^{13}$C-NMR technique (McGready, V. R. et al., in 'Functional studies using NMR', 1987. Springer, London, UK). Cells of E. coli K12 strain 294 (Backman et al. Proc. Natl. Acad. Sci. USA 73: 4174–4178 (1976)) with or without pADC1 were first cultivated in 10 ml LB broth for 6 hours at 37° C. A 0.9 ml sample was then added to the test mixture which further contained 0.05 ml D$_2$O, 0.05 ml 3-$^{13}$C-pyruvate stock solution (Isotec Inc., Miamisburg Ohio 45342, Cat no 83-62024) (to a final concentration of 0.45 mMol). 0.5 ml of this mixture was transferred into a 0.5 cm NMR tube and the NMR spectra were collected overnight (at 90 Mhz on a Bruker AM-360 spectrometer interfaced to an Aspect 3000 computer). The 3-$^{13}$C-pyruvate was used to facilitate the quantification of the reaction products (by $^{13}$C-NMR) and has no special property in the conversion process. No complete conversion of $^{13}$C-pyruvate is obtained with any of the strains under the conditions used. In both cases the formation of acetic acid and lactic acid was observed (FIGS. 3, and 4). However, cells containing pADC1 produced in addition α-acetolactate and acetoin. The production of α-acetolactate starts immediately from the start of the experiment, whereas acetoin appears at a much slower rate. Clearly identifiable acetoin signals are obtained only after some 5 hours of incubation. The production of α-acetolactate in pADC1 containing cells means that these cells contain α-acetolactate synthase activity. E. coli 294 cells lack this activity, as no α-acetolactate was produced. It is therefore concluded that the 4.5 kbp DNA insert in pADC1 carries the active gene for α-ALS, rather than the gene for α-ALD, as stated by Goelling and Stahl (Goelling, D., and Stahl, U., Appl. Environ. Microbiol. 54: 1889-1891 (1988)). Whether the clone in addition contains the gene for α-ALD is not clear. Since α-acetolactate is chemically unstable at pH values lower than 7, the acetoin observed may well be the result of a chemical decarboxylation of α-acetolactate.

Figure 5:
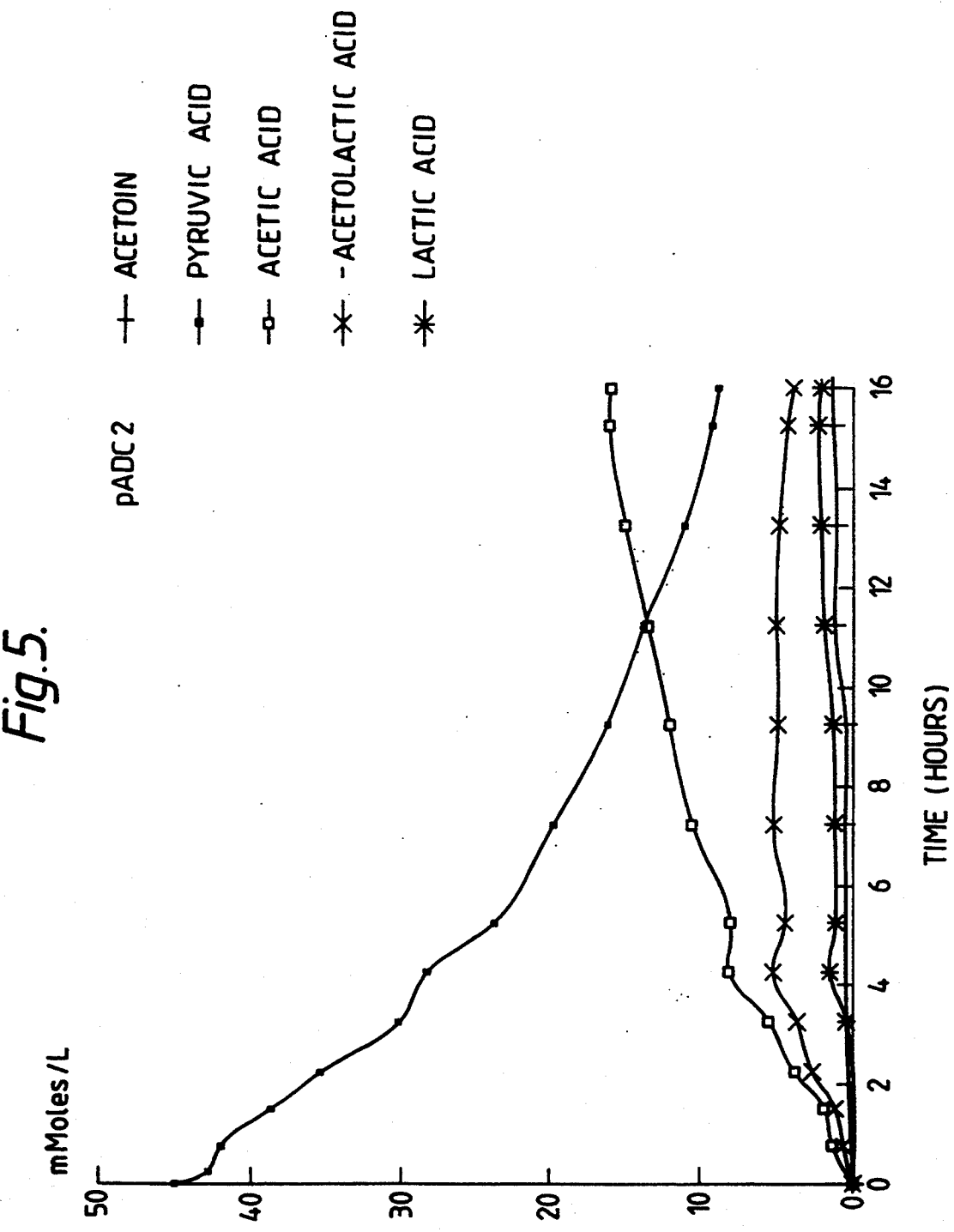
FIG. 5 shows concentrations of $^{13}$C-labelled pyruvate and its metabolites upon fermentation at 37° C. with E. coli 294(pADC2).
Figure 6:
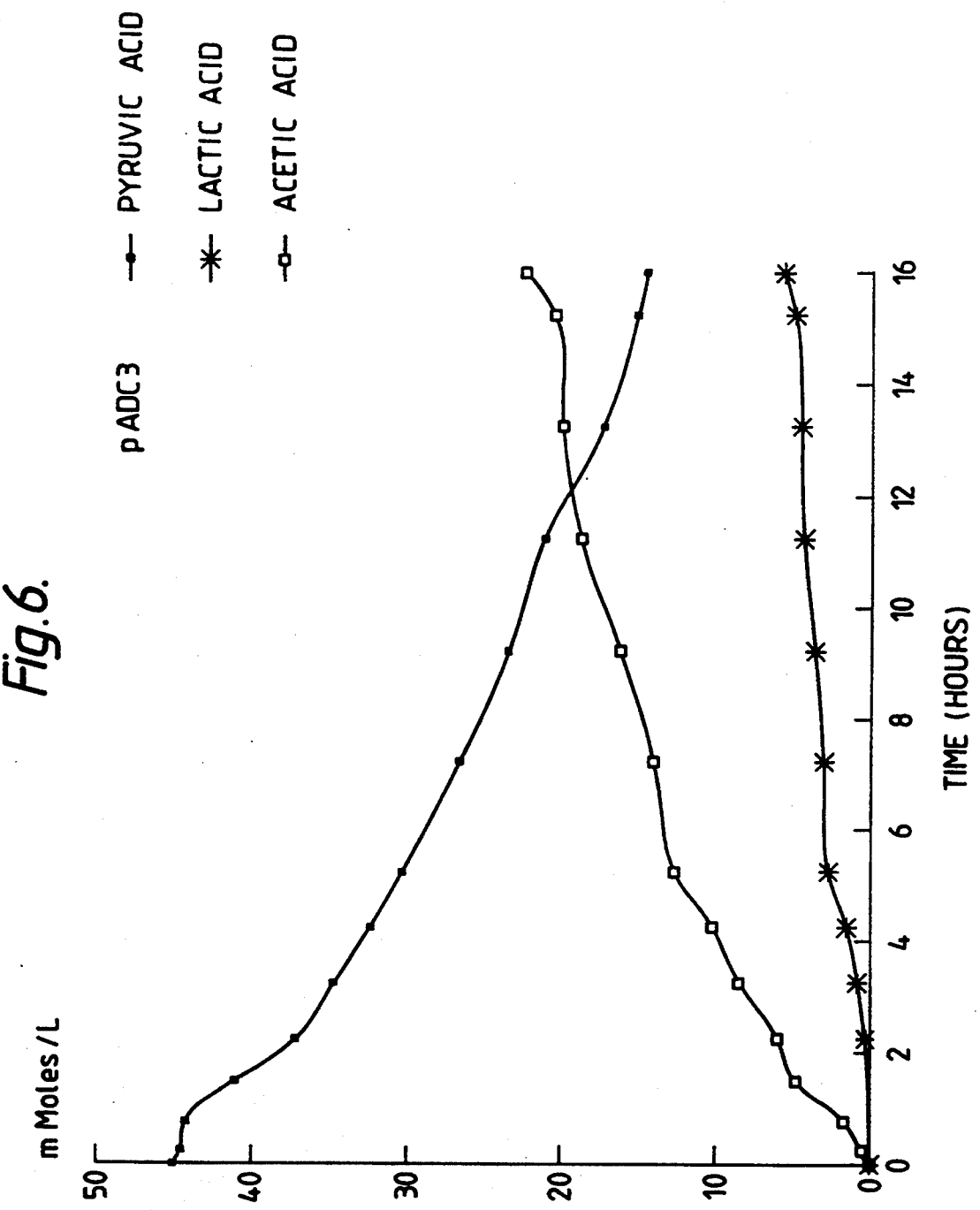
FIG. 6 shows concentrations of $^{13}$C-labelled pyruvate and its metabolites upon fermentation at 37° C. with E. coli 294(pADC3).

Two deletion derivatives of pADC1 were also tested by $^{13}$C NMR analysis. Plasmid pADC2 was obtained by deletion of an approximately 1.3 kbp HindIII fragment from pADC1, while plasmid pADC3 lacked a 2.5 kbp EcoRV fragment (Goelling, D., and Stahl, U., Appl. Environ. Microbiol. 54: 1889-1891 (1988)) (FIG. 2). As the E. coli(pADC1) cells, plasmid pADC2 containing cells showed production of acetic acid, lactic acid and α-acetolactate followed by formation of acetoin at a much slower rate (FIG. 5). Cells containing pADC3 only produced acetic acid and lactic acid, just like the host E. coli 294 (FIG. 6). It means, that the gene for α-ALS must be located after the HindIII site on the 3.0 kbp right half part of the insert (FIG. 2).

EXAMPLE 2

Nucleotide sequence analysis of pADC1

The DNA sequence of part of the 4.5 kbp partial Sau3A DNA fragment, as present on plasmid pADC1, was established by the Sanger dideoxy chain termination procedure (Sanger, F., Nicklen, S., and Coulson, A. R., (1977), Proc. Natl. Acad. Sci. USA, 74, 5463-5467.) with the modifications as described by Biggin et al. (Biggin, M.D. et al., (1983), Proc. Natl. Acad. Sci. USA, 80, 3963-3965), using α-$^{35}$S-dATP (2000 Ci/mmol) and Klenow enzyme (Amersham), ddNTP's (Pharmacia-PL Biochemicals) and dNTP's (Boehringer). The sequencing reaction products were separated on a denaturing polyacrylamide gel with a buffer gradient as described by Biggin et al. (Biggin, M.D. et al., (1983), Proc. Natl. Acad. Sci. USA, 80, 3963-3965). Purified, double-stranded plasmid DNA of pADC1 served as template in the sequence reaction, following the procedure described by Hattori and Sakaki (Hattori, M., and Sakaki, Y. (1986), Anal. Biochem. 152, 232-238). Deoxy-oligonucleotide primers were synthesized on a DNA synthesizer (Applied Biosystems 380A) using the phospho-amidit technique (Barone, A.D. et al., (1984), Nucleic Acid Research, 12, 4051-4061).

The DNA sequence when translated in all possible reading frames revealed a large open reading frame present in the center of insert between the HindIII- and the StuI sites (positions 550-2211, FIG. 1 and SEQ ID NO: 1). The open reading frame encodes a protein which consists of 554 amino acid residues followed by a TGA stop codon (FIG. 1). A ribosome binding site (RBS) is present directly upstream of this open reading frame (positions 534-538, FIG. 1 and SEQ ID NO: 1). Further upstream of the open reading frame a promoter is located. The sequences of its −35 (TTGTAA) and −10 (TAAAAT) (SEQ ID NO: 1 and FIG. 1, positions 458-463, and 481-486, respectively) correspond to those of constitutive promoters of gram-positive bacteria. Comparison of the primary structure of the gene product with protein sequences present in a protein data bank (EMBL Data Library), revealed sequence similarities with the α-acetolactate synthase enzymes from both E. coli (Squires et al. Nucleic Acid Res. 11:5299-5313 (1983)) and Saccharomyces cerevisiae (Falco et al. Nucleic Acid Res. 13: 4011-4027 (1985)). The GAP programme mentioned hereinbefore produced similarity percentages of 51% and 54%, respectively. Together with the NMR data described above (Example 1) it shows that the open reading frame is indeed the gene for α-ALS from L. diacetylactis.

EXAMPLE 3

Expression of α-ALS in Bacillus subtilis

To enhance α-ALS activity in B. subtilis, the 2.0 kbp HindIII-StuI fragment of pADC1, containing the complete α-acetolactate synthase gene, was transferred into the broad host range plasmid pGKV41, a derivative of the L. lactis plasmid pGKV410 (Van der Vossen J.M.B.M. PhD thesis, Rijksuniversiteit Groningen, 1988). Therefore, the said HindIII-StuI fragment was ligated in plasmid pGKV41 that was first digested with HindIII and SmaI to obtain plasmid pUR5400. The ligation mixture was used to transform B. subtilis DB105 protoplasts (Leenhouts, K., Kok J., and Venema, G., 1990. Appl. Environ. Microbiol. 56: 2726-2735) selecting for erythromycin-resistant colonies.

One of these transformants and DB105 control cells were tested by $^{13}$C NMR analysis. After cultivating for 18 hours in LB broth supplemented with or without (control cells) 5 μg/ml erythromycin at 37° C. the cells were harvested by centrifugation and washed with physiological salt solution. Subsequently the cells were taken up in phosphate buffer 0.002 mole/1 at pH 7.0 and homogenized ultrasonically in the presence of acid-washed glass beads (<150 microns). The complete lysate was used to convert 36 μmole 3-$^{13}$C-pyruvate which was contained in 1 ml reaction volume. The reaction mixture furthermore contained 100 μl D$_2$O (for $^{13}$C-NMR purposes), thiamine pyrophosphate (0.25 μmole) and MgSO$_4$ (1.5 μmole) in 0.06 mol/1 phosphate buffer at pH 6.5. The protein content of either lysate or extract was standardized at 0.9 mg protein/ml in the experiment.

Figure 7:
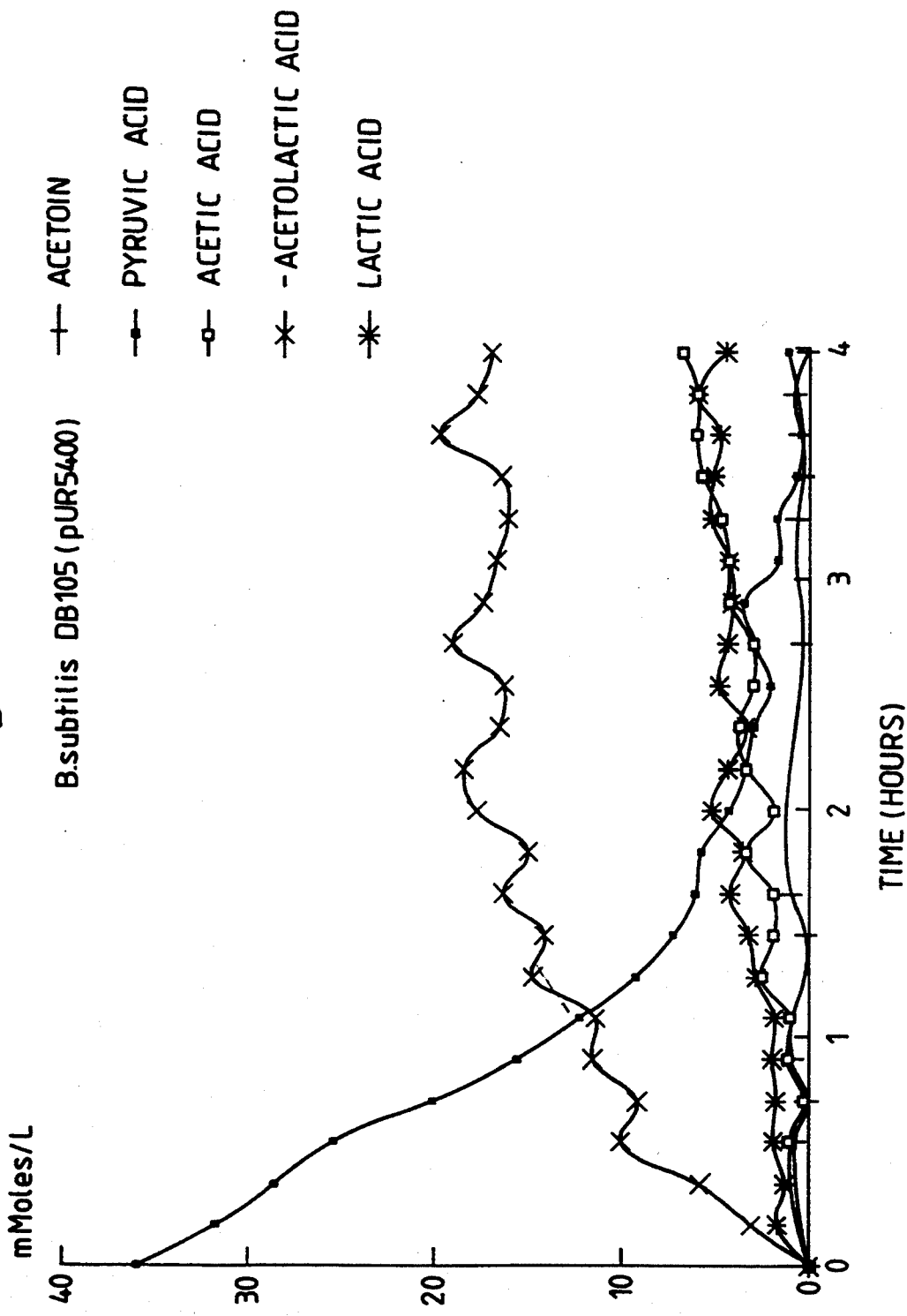
FIG. 7 shows concentrations of $^{13}$C-labelled pyruvate and its metabolites obtained during incubation with a lysate of B. subtilis (pUR5400).
Figure 8:
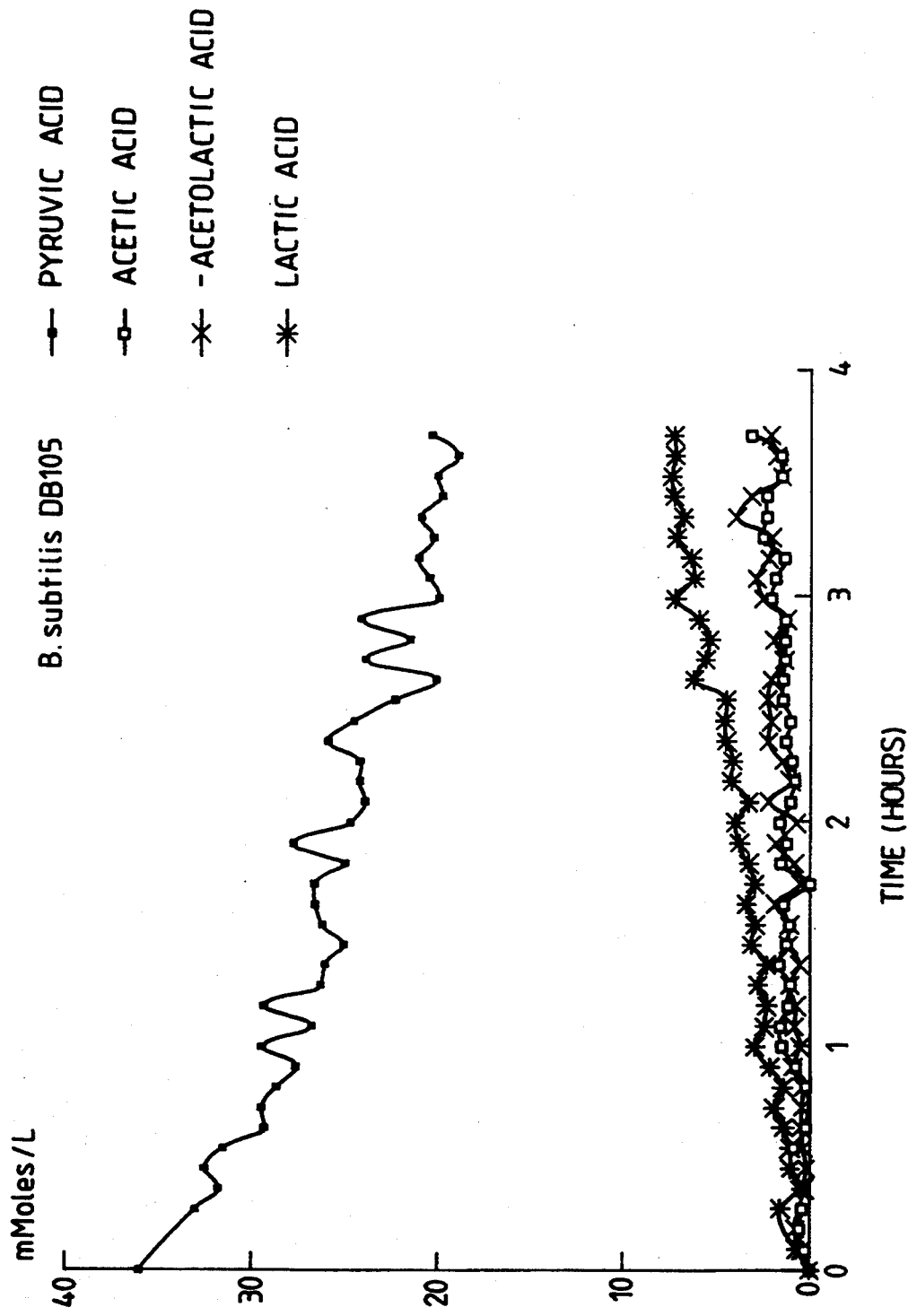
FIG. 8 shows concentrations of $^{13}$C-labelled pyruvate and its metabolites obtained during incubation with a lysate of B. subtilis.

In the lysates of DB105 cells containing pUR5400 pyruvate was converted very rapidly and almost quantitatively into α-acetolactate during the first two hours. In addition, lactate, acetate and at much lower rate acetoin were formed (FIG. 7). In lysates of the non-transformed DB105 host cells pyruvate was converted at a much slower rate yielding low, but detectable levels of lactate, acetate and α-acetolactate only (FIG. 8).

EXAMPLE 4

Expression of α-ALS in L. lactis subsp. lactis.

The complete α-acetolactate synthase gene was also cloned in the lactococcal plasmid vector pNZ123 (EPA 0 228 726 A1). From plasmid pADC1 the 2.0 kbp HindIII-StuI fragment was isolated, treated with Klenow enzyme to fill in the 3'-recessed ends, and subsequently ligated into pNZ123 which was cut with the restriction enzyme ScaI, resulting in pUR5401. The ligation mixture was used to transform E. coli 294 cells, selecting for transformants on LB plates containing 100 μg/ml chloramphenicol. From the obtained transformants plasmid DNA was isolated, checked by restriction enzyme analysis, and subsequently used to electrotransform L. lactis. subsp. lactis (L. lactis) MG1363 cells (Leenhouts, K., Kok J., and Venema, G., 1990. Appl. Environ. Microbiol. 56: 2726–2735). From the obtained transformants one was tested by $^{13}$C-NMR analysis (together with MG1363 control cells).

Cells of L. lactis strain MG1363 with and without pUR5401 were cultivated in M17 broth which contained 1% (w/v) of glucose as carbohydrate. After growth cells were treated as described in the previous example (see above).

Figure 9:
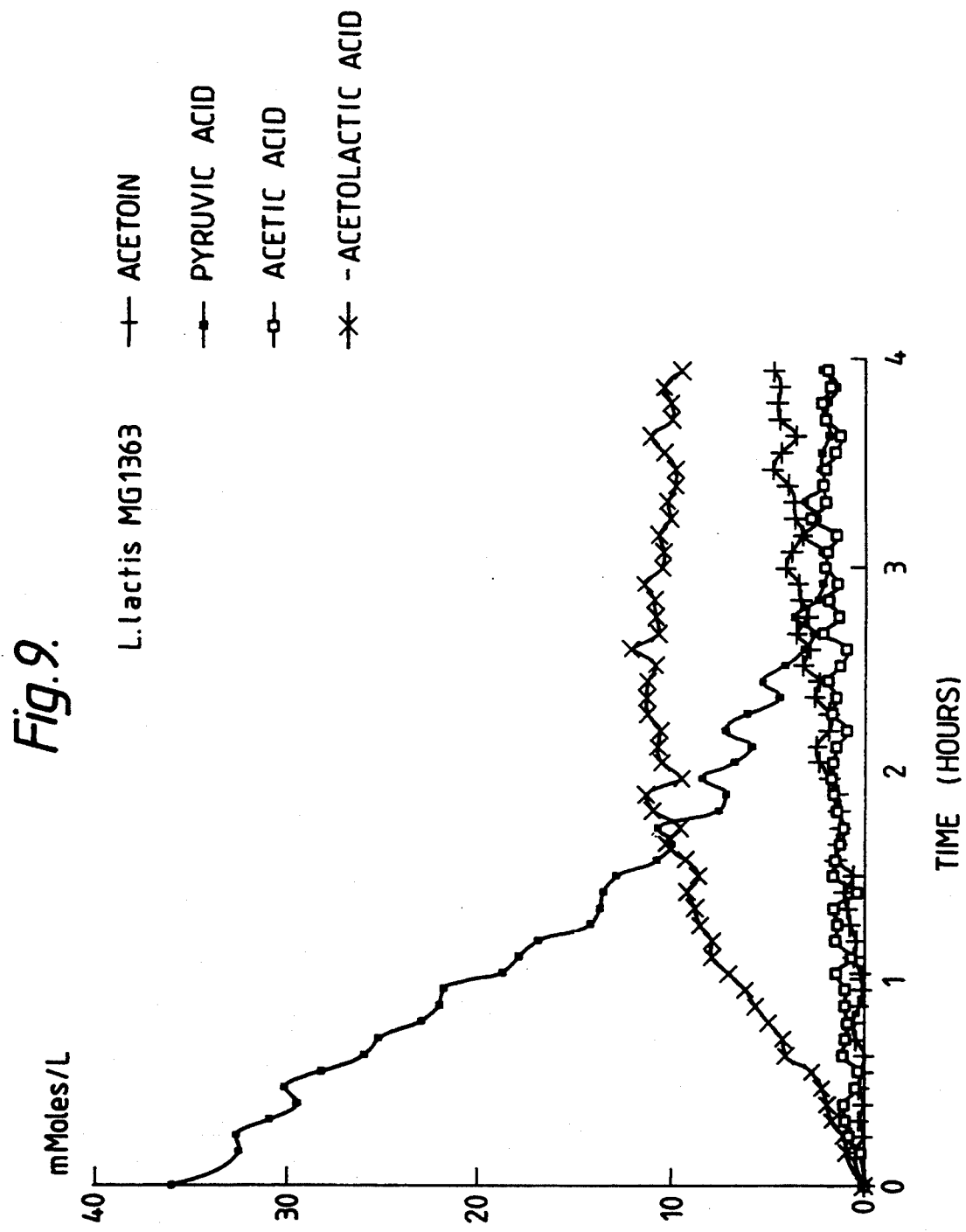
FIG. 9 shows concentrations of $^{13}$C-labelled pyruvate and its metabolites obtained during incubation with a lysate of L. lactis MG1363.
Figure 10:
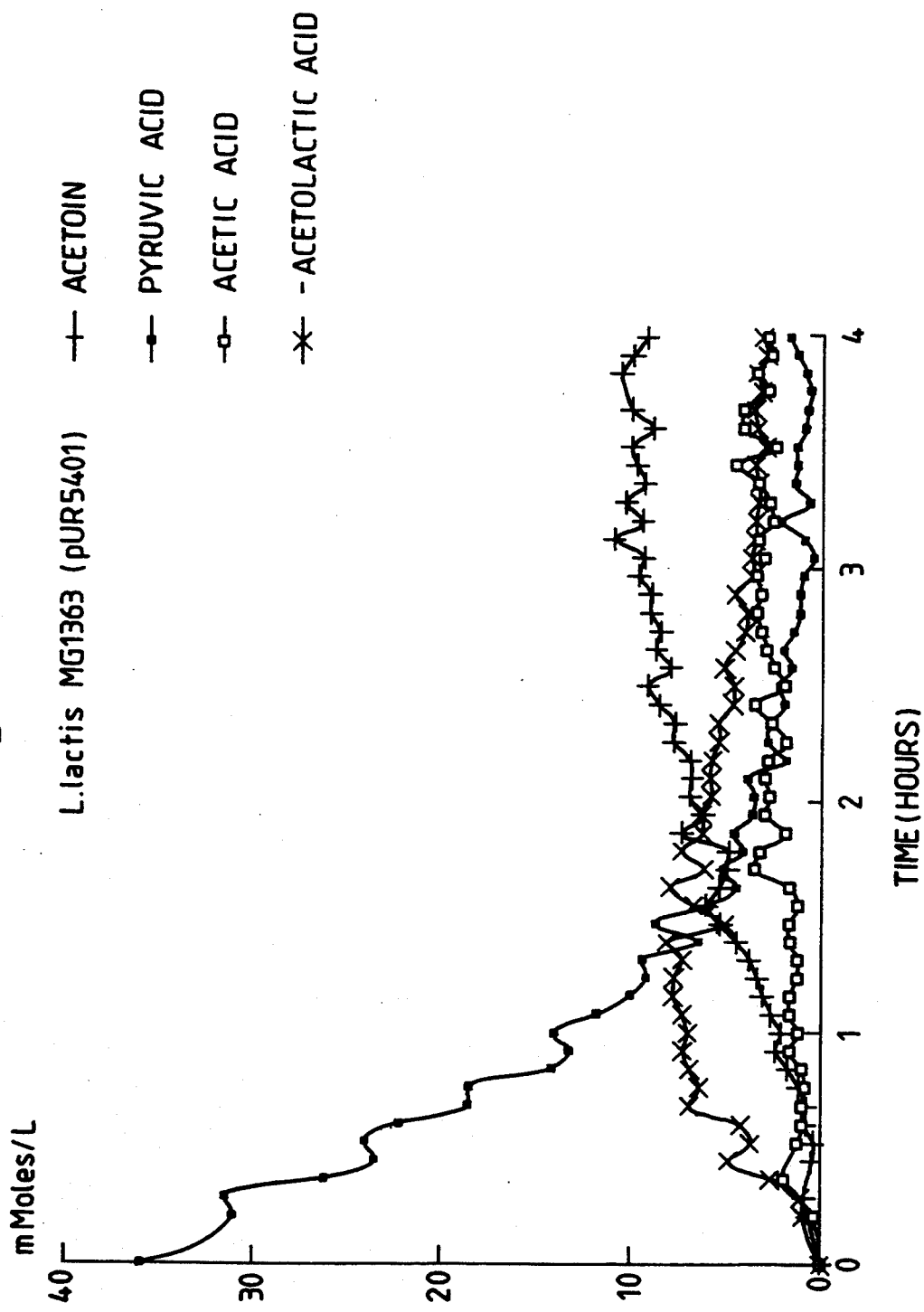
FIG. 10 shows concentrations of $^{13}$C-labelled pyruvate and its metabolites obtained during incubation with a lysate of L. lactis MG1363(pUR5401).

In lysates of the non-transformed MG1363 host cells pyruvate was converted at a rate of 0.118 μmole/mg protein/min yielding about 10 mM α-acetolactate, and low levels of acetate and acetoin (FIG. 9). In lysates of MG1363(pUR5401) cells pyruvate was converted more rapidly, at a rate of 0.172 μmole/mg protein/min yielding about 8 mM α-acetolactate (FIG. 10). However, acetoin is also formed at a higher rate than in non-transformed cells. The acetoin formation is concomittant with a decline of α-acetolactate levels and is most probably the result of α-ALD activity present in the lysate.

EXAMPLE 5

Expression of α-ALS in L. lactis subsp. lactis biovar diacetylactis SD803.

Expression of α-ALS was also studied in L. lactis subsp. lactis biovar diacetylactis (L. diacetylactis) strain SD803, a natural mutant defective in α-ALD activity (EP 0 247 646 B1). For this purpose the complete α-acetolactate synthase gene was transferred into the broad host range cloning vector pIL253 (Simon, D., and Chopin, A., Biochimie 70: 559–566 (1988)). The 4.1 kbp PstI-NruI fragment of pADC1 with the complete α-ALS gene was isolated, and ligated in plasmid pIL253 that was first digested with restriction enzymes PstI and SmaI. In this way plasmid pUR5402 was obtained. The ligation mixture was used to transform B. subtilis DB105 protoplasts (Leenhouts, K., Kok J., and Venema, G., 1990. Appl. Environ. Microbiol. 56: 2726–2735) selecting for erythromycin-resistant colonies. From the obtained transformant cells plasmid DNA was isolated, checked by restriction enzyme analysis, and a correct recombinant plasmid was subsequently used to electrotransform L. diacetylactis SD803 cells (Leenhouts, K., Kok J., and Venema, G., 1990. Appl. Environ. Microbiol. 56: 2726–2735). From the obtained transformants one was tested by $^{13}$C-NMR analysis (together with SD803 control cells).

Cells of L. diacetylactis strain SD803 with and without pUR5402 were cultivated in M17 broth which contained 1% (w/v) of glucose as carbohydrate. After growth cells were treated as described in example 3 (see above).

Figure 11:
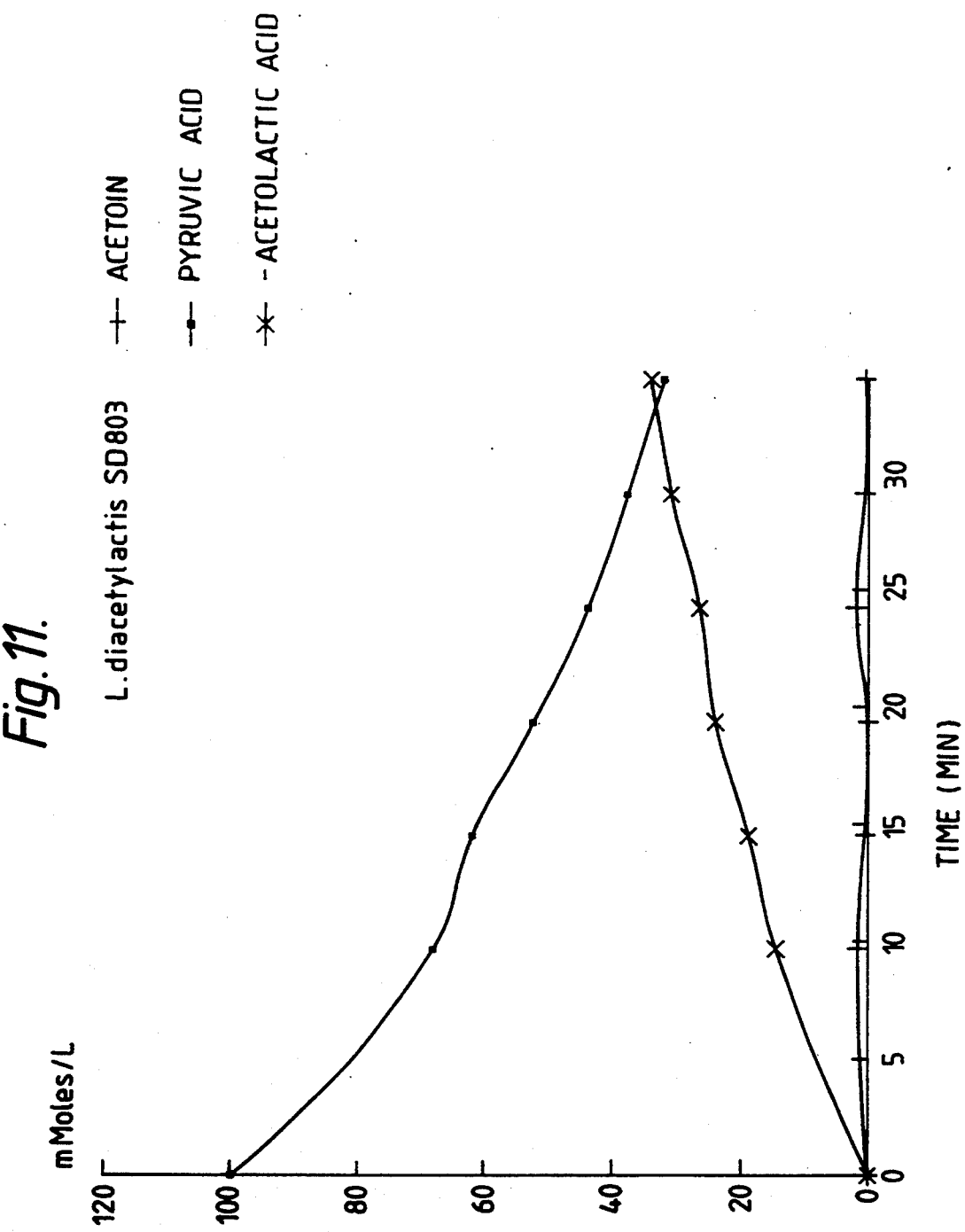
FIG. 11 shows concentrations of $^{13}$C-labelled pyruvate and its metabolites obtained during incubation with a lysate of L. diacetylactis SD803.
Figure 12:
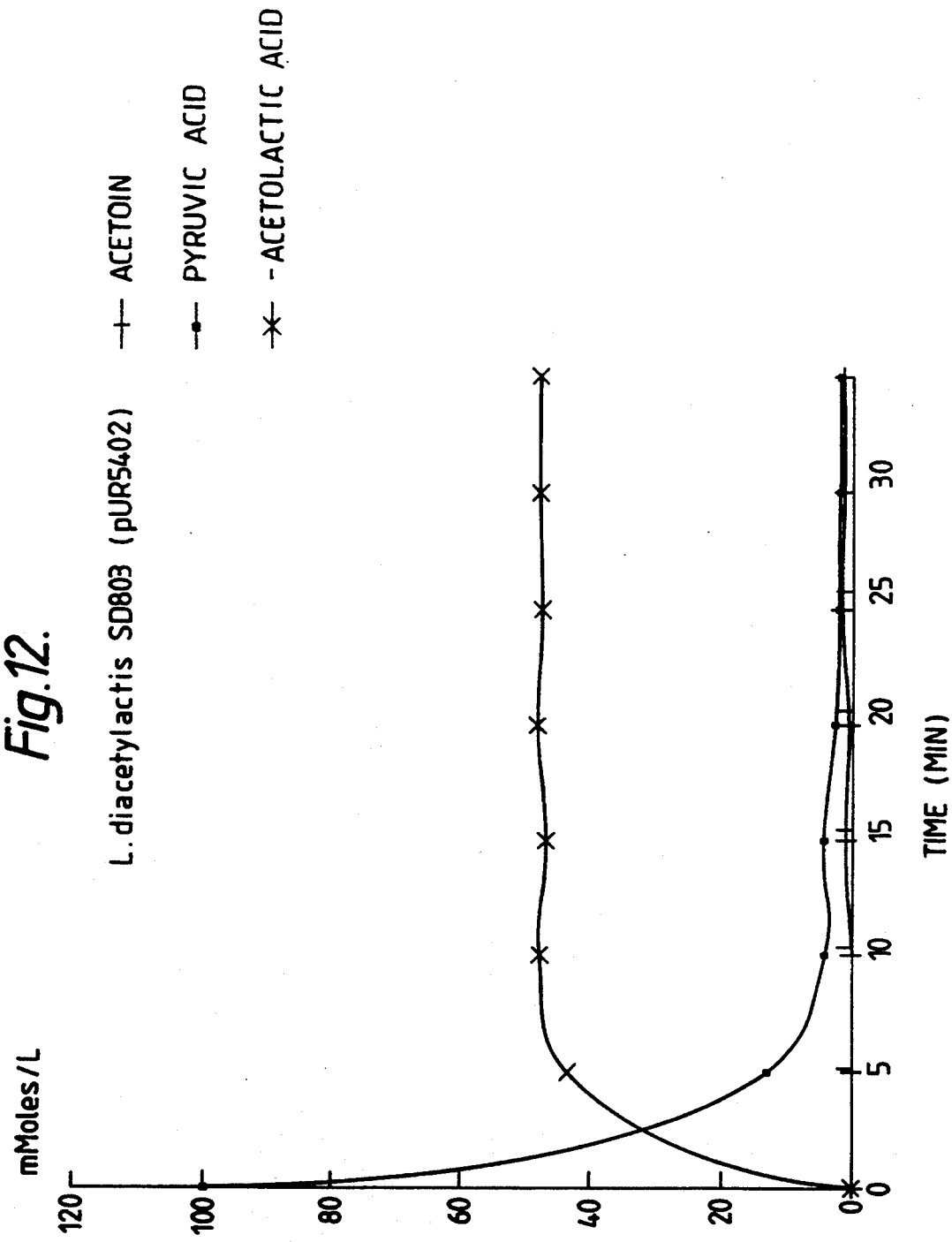
FIG. 12 shows concentrations of $^{13}$C-labelled pyruvate and its metabolites obtained during incubation with a lysate of L. diacetylactis SD803(pUR5402).

In lysates of the non-transformed SD803 cells pyruvate was converted almost completely into α-acetolactate, at a rate of 0.428 μmole/mg protein/min. Only very low levels of acetoin could be detected, whereas formation of lactate and acetate was not observed at all (FIG. 11). In lysates of SD803(pUR5402) cells the conversion of pyruvate resulted in a quantitative formation of α-acetolactate, but at a much higher rate (3.49 μmole/mg protein/min) than in the non-transformed SD803 cells (FIG. 12). Again, no lactate or acetate was formed and only very low levels of acetoin were detected.

EXAMPLE 6

Expression of α-acetolactate synthase by whole cells of Lactococcus lactis subsp. lactis biovar diacetylactis This experiment was carried out to study the conversion of pyruvic acid by whole cells of Lactococcus lactis subsp. lactis biovar diacetylactis, which contain multiple copies of the α-acetolactate synthase gone. Therefore, strain SD803 was transformed with plasmids pUR5400 and pUR5402 (see Examples 3–5). The non-transformed 8D803 was used as the reference strain. The strains were cultivated overnight at 25° C. in M17 broth which contained 1% (wt/vol) of lactose as carbohydrate and which was supplemented with 0.2% (wt/vol) of sodium citrate.

The rate of conversion of pyruvate and the type of reaction products formed by these strains was studied as described in Example 1. The final concentration of odium[3-$^{13}$C]pyruvate in the reaction liquid was 45.5 mmol/litre. 0.8 ml of the reaction mixture was transferred into a NMR tube which had a diameter of 0.5 cm, and the conversion of the pyruvate was monitored in the NMR apparatus at 30° C.

For all three strains, the products formed were identical. However, it appeared that the rate at which the metabolites α-acetolactic acid and lactic acid were formed, was different. The rate of formation of α-acetolactic acid was significantly increased with the transformed strains, while the rate of formation of lactic acid was significantly decreased (sea Table 1). Moreover, after 90 min reaction time the conversion resulted in considerably higher concentrations of α-acetolactic acid and lower concentrations of lactic acid in the transformed strains as compared to the reference strain (see Table 2).

TABLE 1

Rate of pyruvate utilisation and of metabolite formation, expressed as mmol utilized/formed per minute. The results were calculated on the basis of a cell culture with an O.D.$_{610}$ of 3.45.

| Strain | Pyruvate | α-Acetolactic acid | Lactic acid |
|---|---|---|---|
| SD803 | −0.35 | 0.11 | 0.14 |
| SD803 (pUR5400) | −0.33 | 0.15 | 0.08 |
| SD803 (pUR5402) | −0.33 | 0.14 | 0.04 |

TABLE 2

Concentrations (mmol) of substrate and metabolites after 90 minutes reaction time.

| Strain | Pyruvate | α-Acetolactic acid | Acetoin | Lactic acid |
|---|---|---|---|---|
| SD803 | 20.24 | 6.33 | 0.09 | 11.93 |
| SD803 (pUR5400) | 19.00 | 9.13 | 0.34 | 8.18 |
| SD803 (pUR5402) | 20.63 | 8.93 | 0.37 | 5.49 |

SEQUENCE LISTING

5,420,021

11 12

-continued ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2538 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CTGCAGCAGA  ACGTTATCTC  GTGGATGCTT  TAAATTTACC  AGAATTACAT  GACGAAACAG    60
TCTTTTTGCT  TGCTAATTTA  TACTTCAACG  AAGAAGATTT  TGAAGCTGTC  ATTAATCTTG   120
AAGAGCTTTT  AGAAGATGAA  CATTTATTAG  CTAAATGGCT  TTTTGCAGGA  GCACATAAAG   180
CTTTGGAAAA  TGATTCTGAA  GCGGCTGCTT  TGTATGAAGA  ACTCATTCAA  ACCAATCTGT   240
CAGAGAATCC  AGAGTTTTTA  GAAGACTATA  TTGATTTTCT  TAAAGAAATT  GGTCAAATTT   300
CTAAAACAGA  ACCAATTATT  GAACAATATT  TGGAACTTGT  TCCAGATGAT  GAAAATATGA   360
GAAATTTACT  GACAGACTTA  AAAAATAATT  ACTGACAAAG  CTGTCAGTAA  TTATTTTAT    420
TGTAAGCTAG  AAAATTCAAA  AACTTGCGTC  AAAATAATTG  TAAAAGGTTC  TATTATCTGA   480
TAAAATGATT  GTGAAGTAAT  CCAAGAGATT  ATGAAATATG  AATTAGAACA  AATAGAGGTA   540
AAATAAAAAA  TGTCTGAGAA  ACAATTTGGG  GCGAACTTGG  TTGTCGATAG  TTTGATTAAC   600
CATAAAGTGA  AGTATGTATT  TGGGATTCCA  GGAGCAAAAA  TTGACCGGGT  TTTTGATTTA   660
TTAGAAAATG  AAGAAGGCCC  TCAAATGGTC  GTGACTCGTC  ATGAGCAAGG  AGCTGCTTTC   720
ATGGCTCAAG  CTGTCGGTCG  TTTAACTGGC  GAACCTGGTG  TAGTAGTTGT  TACGAGTGGG   780
CCTGGTGTAT  CAAACCTTGC  GACTCCGCTT  TTGACCGCGA  CATCAGAAGG  TGATGCTATT   840
TTGGCTATCG  GTGGACAAGT  TAAACGAAGT  GACCGTCTTA  ACGTGCGCA   CCAATCAATG   900
GATAATGCTG  GAATGATGCA  ATCAGCAACA  AAATATTCAG  CAGAAGTTCT  TGACCCTAAT   960
ACACTTCTG   AATCAATTGC  CAACGCTTAT  CGTATTGCAA  ATCAGGACA   TCCAGGTGCA  1020
ACTTTCTTAT  CAATCCCCCA  AGATGTAACG  GATGCCGAAG  TATCAATCAA  AGCCATTCAA  1080
CCACTTTCAG  ACCCTAAAAT  GGGGAATGCC  TCTATTGATG  ACATTAATTA  TTTAGCACAA  1140
GCAATTAAAA  ATGCTGTATT  GCCAGTAATT  TTGGTTGGAG  CTGGTGCTTC  AGATGCTAAA  1200
GTCGCTTCAT  CCTTGCGTAA  TCTATTGACT  CATGTTAATA  TTCCTGTCGT  TGAAACATTC  1260
CAAGGTGCAG  GGGTTATTTC  ACATGATTTA  GAACATACTT  TTTATGGACG  TATCGGTCTT  1320
TTCCGCAATC  AACCAGGCGA  TATGCTTCTG  AAACGTTCTG  ACCTTGTTAT  TGCTGTTGGT  1380
TATGACCCAA  TTGAATATGA  AGCTCGTAAC  TGGAATGCAG  AAATTGATAG  TCGAATTATC  1440
GTTATTGATA  ATGCCATTGC  TGAAATTGAT  ACTTACTACC  AACCAGAGCG  TGAATTAATT  1500
GGTGATATCG  CAGCAACATT  GGATAATCTT  TTACCAGCTG  TTCGTGGCTA  CAAAATTCCA  1560
AAAGGAACAA  AAGATTATCT  CGATGGCCTT  CATGAAGTTG  CTGAGCAACA  CGAATTTGAT  1620
ACTGAAAATA  CTGAAGAAGG  TAGAATGCAC  CCTCTTGATT  TGGTCAGCAC  TTTCCAAGAA  1680
ATCGTCAAGG  ATGATGAAAC  AGTAACCGTT  GACGTAGGTT  CACTCTACAT  TGGATGGCA   1740
CGTCATTTCA  AATCATACGA  ACCACGTCAT  CTCCTCTTCT  CAAACGGAAT  GCAAACACTC  1800
GGAGTTGCAC  TTCCTTGGGC  AATTACAGCC  GCATTGTTGC  GCCCAGGTAA  AAAAGTTTAT  1860
TCACACTCTG  GTGATGGAGG  CTTCCTTTTC  ACAGGGCAAG  AATTGGAAAC  AGCTGTACGT  1920
TTGAATCTTC  CAATCGTTCA  AATTATCTGG  AATGACGGCC  ATTATGATAT  GGTTAAATTC  1980
```

```
CAAGAAGAAA TGAAATATGG TCGTTCAGCA GCCGTTGATT TTGGCTATGT TGATTACGTA    2040

AAATATGCTG AAGCAATGAG AGCAAAAGGT TACCGTGCAC ACAGCAAAGA AGAACTTGCT    2100

GAAATTCTCA AATCAATCCC AGATACTACT GGACCGGTGG TAATTGACGT TCCTTTGGAC    2160

TATTCTGATA ACATTAAATT AGCAGAAAAA TTATTGCCTG AAGAGTTTTA TTGATTACAA    2220

TCAAGCAATT TGTGGCATAA CAAAATAAAA GAAGAAGGCC TTGAACACCT AAGCGTTCAG    2280

GGCCTTTTTT TGTGAAATAA ATTAGATGAA ATTTACAATG AGTTTGTGA AACTAGCTTC     2340

TAGTTTGTGA AAAATTGCCT ATAATTGCCG AATAAAAATA CCCATTTACC ACTCCAAGAG    2400

GATGCTTCAA ATTAGCTAAA TACCCGTTTT AGAGGATGCG TAAAACAAC AAAAGAGGAT     2460

GAGTATAGAA CGATAAAACT TTTTTATGAT AGGTTGAGAG AATTGAATAT AAAATATAAT    2520

AAGTAGAAGG CAGCAATT                                                  2538
```

(2) INFORMATION FOR SEQ ID NO:2:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Ser Glu Lys Gln Phe Gly Ala Asn Leu Val Val Asp Ser Leu Ile
 1               5                  10                  15

Asn His Lys Val Lys Tyr Val Phe Gly Ile Pro Gly Ala Lys Ile Asp
                20                  25                  30

Arg Val Phe Asp Leu Leu Glu Asn Glu Gly Pro Gln Met Val Val
         35                  40                  45

Thr Arg His Glu Gln Gly Ala Ala Phe Met Ala Gln Ala Val Gly Arg
     50                  55                  60

Leu Thr Gly Glu Pro Gly Val Val Val Thr Ser Gly Pro Gly Val
 65                  70                  75                  80

Ser Asn Leu Ala Thr Pro Leu Leu Thr Ala Thr Ser Glu Gly Asp Ala
                 85                  90                  95

Ile Leu Ala Ile Gly Gly Gln Val Lys Arg Ser Asp Arg Leu Lys Arg
                100                 105                 110

Ala His Gln Ser Met Asp Asn Ala Gly Met Met Gln Ser Ala Thr Lys
         115                 120                 125

Tyr Ser Ala Glu Val Leu Asp Pro Asn Thr Leu Ser Glu Ser Ile Ala
    130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
                180                 185                 190

Asn Tyr Leu Ala Gln Ala Ile Lys Asn Ala Val Leu Pro Val Ile Leu
            195                 200                 205

Val Gly Ala Gly Ala Ser Asp Ala Lys Val Ala Ser Ser Leu Arg Asn
    210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
                245                 250                 255
```

-continued

| | | | | | | | | | | | | | | |
|---|---|---|---|---|---|---|---|---|---|---|---|---|---|---|
| Leu | Phe | Arg | Asn 260 | Gln | Pro | Gly | Asp | Met 265 | Leu | Leu | Lys | Arg | Ser 270 | Asp | Leu |
| Val | Ile | Ala 275 | Val | Gly | Tyr | Asp | Pro 280 | Ile | Glu | Tyr | Glu | Ala 285 | Arg | Asn | Trp |
| Asn | Ala 290 | Glu | Ile | Asp | Ser | Arg 295 | Ile | Ile | Val | Ile | Asp 300 | Asn | Ala | Ile | Ala |
| Glu 305 | Ile | Asp | Thr | Tyr | Tyr 310 | Gln | Pro | Glu | Arg | Glu 315 | Leu | Ile | Gly | Asp | Ile 320 |
| Ala | Ala | Thr | Leu | Asp 325 | Asn | Leu | Leu | Pro | Ala 330 | Val | Arg | Gly | Tyr | Lys 335 | Ile |
| Pro | Lys | Gly | Thr 340 | Lys | Asp | Tyr | Leu | Asp 345 | Gly | Leu | His | Glu | Val 350 | Ala | Glu |
| Gln | His | Glu 355 | Phe | Asp | Thr | Glu | Asn 360 | Thr | Glu | Glu | Gly | Arg 365 | Met | His | Pro |
| Leu | Asp 370 | Leu | Val | Ser | Thr | Phe 375 | Gln | Glu | Ile | Val | Lys 380 | Asp | Asp | Glu | Thr |
| Val 385 | Thr | Val | Asp | Val | Gly 390 | Ser | Leu | Tyr | Ile | Trp 395 | Met | Ala | Arg | His | Phe 400 |
| Lys | Ser | Tyr | Glu | Pro 405 | Arg | His | Leu | Leu | Phe 410 | Ser | Asn | Gly | Met | Gln 415 | Thr |
| Leu | Gly | Val | Ala 420 | Leu | Pro | Trp | Ala | Ile 425 | Thr | Ala | Ala | Leu | Leu 430 | Arg | Pro |
| Gly | Lys | Lys 435 | Val | Tyr | Ser | His | Ser 440 | Gly | Asp | Gly | Gly | Phe 445 | Leu | Phe | Thr |
| Gly | Gln 450 | Glu | Leu | Glu | Thr | Ala 455 | Val | Arg | Leu | Asn | Leu 460 | Pro | Ile | Val | Gln |
| Ile 465 | Ile | Trp | Asn | Asp | Gly 470 | His | Tyr | Asp | Met | Val 475 | Lys | Phe | Gln | Glu | Glu 480 |
| Met | Lys | Tyr | Gly | Arg 485 | Ser | Ala | Ala | Val | Asp 490 | Phe | Gly | Tyr | Val | Asp 495 | Tyr |
| Val | Lys | Tyr | Ala 500 | Glu | Ala | Met | Arg | Ala 505 | Lys | Gly | Tyr | Arg | Ala 510 | His | Ser |
| Lys | Glu | Glu 515 | Leu | Ala | Glu | Ile | Leu 520 | Lys | Ser | Ile | Pro | Asp 525 | Thr | Thr | Gly |
| Pro | Val 530 | Val | Ile | Asp | Val | Pro 535 | Leu | Asp | Tyr | Ser | Asp 540 | Asn | Ile | Lys | Leu |
| Ala 545 | Glu | Lys | Leu | Leu | Pro 550 | Glu | Glu | Phe | Tyr | | | | | | |

We claim:

1. Process for the production of α-acetolactate and/or diacetyl, wherein a recombinant micro-organism containing a sequence encoding an α-acetolactate synthase and involved in acetoin and/or diacetyl formation is incubated in a medium containing an α-acetolactate precursor, the micro-organism being selected from the genera Lactococcus, Streptococcus, Lactobacillus, Leuconostoc, Pediococcus, Bacillus, Bifidobacterium, Brevibacterium, Micrococcus, Propionibacterium, Staphylococcus, Gluconobacter, Acetobacter, Vibrio, Corynebacterium and Zymomonas, wherein the α-acetolactate synthase-encoding sequence comprises the nucleotide sequence essentially corresponding to the sequence 550–2211 of SEQ ID NO: 1.

2. Process according to claim 1, wherein the α-acetolactate precursor comprises citrate, pyruvate and/or precursors thereof.

3. Process according to claim 1, wherein the micro-organism has a substantially reduced α-acetolactate decarboxylase activity.

4. Recombinant vector comprising a nucleotide sequence coding for an enzyme, which vector upon transfer into a host micro-organism enables expression of the nucleotide sequence in the host micro-organism, wherein the enzyme has α-acetolactate synthase activity and comprises an amino acid sequence which essentially corresponds to the sequence given in SEQ ID NO: 2, wherein the recombinant vector comprises:

(a) a double-stranded DNA (ds-DNA) coding for α-acetolactate synthase starting with a translational initiation codon, bound to the 5'-end of the coding region of the plus strand of the ds-DNA;

(b) an expression regulon situated upstream of the plus strand of the ds-DNA;

(c) a translational stop codon, bound to the 3'-end of the coding region of the plus strand of the ds-DNA, optionally followed by:
(d) a transcription termination sequence; and
(e) a nucleotide sequence which facilitates integration of the gene coding for α-acetolactate synthase into a host genome.

5. Micro-organism capable of producing α-acetolactate synthase, wherein the micro-organism is selected from the group consisting of (i) a host micro-organism in which a recombinant vector comprising a nucleotide sequence has been introduced, which vector upon transfer into a host micro-organism enables expression of the nucleotide sequence in the host micro-organism, which nucleotide encodes an enzyme having α-acetolactate synthase activity and comprising an amino acid sequence which essentially corresponds to the sequence given in SEQ ID NO: 2, and (ii) the progeny obtained from such a host micro-organism, said host micro-organism being selected from the genera Lactococcus, Streptococcus, Lactobacillus, Leuconostoc, Pediococcus, Bacillus, Bifidobacterium, Brevibacterium, Micrococcus, Propionibacterium, Staphylococcus, Gluconobacter, Acetobacter, Vibrio, Corynebacterium and Zymomonas.

6. Micro-organism according to claim 5, wherein the micro-organism is food-grade and selected from the genera Lactococcus, Streptococcus, Lactobacillus, Leuconostoc, Bifidobacterium, Brevibacterium and Propionibacterium.

7. Micro-organism according to claim 5, wherein the micro-organism has a substantially reduced α-acetolactate decarboxylase activity.

8. The process according to claim 1, wherein the micro-organism is food-grade and selected from the genera Lactococcus, Streptococcus, Lactobacillus, Leuconostoc, Bifidobacterium, Brevibacterium and Propionibacterium.

* * * * *